US012806137B2

(12) United States Patent
Mangalathillam et al.

(10) Patent No.: US 12,806,137 B2
(45) Date of Patent: Nov. 24, 2026

(54) NANOLIPID CARRIER BASED FORMULATION FOR BRAIN DELIVERY THROUGH INTRANASAL ROUTE AND ITS PREPARATION PROCESS

(71) Applicant: AMRITA SCHOOL OF PHARMACY, AMRITA VISHWA VIDYAPEETHAM, Kochi (IN)

(72) Inventors: Sabitha Mangalathillam, Kochi (IN); Sreeja Chandrasekharan Nair, Kochi (IN); Kollencheri Puthenveettil Vinayan, Kochi (IN)

(73) Assignee: AMRITA SCHOOL OF PHARMACY, AMRITA VISHWA VIDYAPEETHAM, Kochi (IN)

( * ) Notice: Subject to any disclaimer, the term of this patent is extended or adjusted under 35 U.S.C. 154(b) by 667 days.

(21) Appl. No.: 18/108,542

(22) Filed: Feb. 10, 2023

(65) Prior Publication Data

US 2024/0108573 A1 Apr. 4, 2024

(30) Foreign Application Priority Data

Sep. 30, 2022 (IN) ............................. 202241056432

(51) Int. Cl.

| | |
|---|---|
| ***A61K 9/00*** | (2006.01) |
| ***A61K 9/1277*** | (2025.01) |
| ***A61K 31/4166*** | (2006.01) |
| ***A61K 47/10*** | (2017.01) |
| ***A61K 47/12*** | (2006.01) |
| ***A61K 47/28*** | (2006.01) |
| ***A61P 25/08*** | (2006.01) |
| ***B82Y 5/00*** | (2011.01) |
| ***B82Y 30/00*** | (2011.01) |
| ***B82Y 40/00*** | (2011.01) |

(52) U.S. Cl.

CPC .......... *A61K 9/0043* (2013.01); *A61K 9/1277* (2013.01); *A61K 31/4166* (2013.01); *A61K 47/10* (2013.01); *A61K 47/12* (2013.01); *A61K 47/28* (2013.01); *A61P 25/08* (2018.01); *B82Y 5/00* (2013.01); *B82Y 30/00* (2013.01); *B82Y 40/00* (2013.01)

(58) Field of Classification Search

None

See application file for complete search history.

(56) References Cited

U.S. PATENT DOCUMENTS

| | | | |
|---|---|---|---|
| 6,150,420 | A | 11/2000 | Houdi et al. |
| 9,550,036 | B2 | 1/2017 | Hoekman et al. |
| 2021/0269513 | A1 | 9/2021 | Glassy et al. |

FOREIGN PATENT DOCUMENTS

| | | |
|---|---|---|
| CN | 102552105 A | 7/2012 |

OTHER PUBLICATIONS

Thi-Thao-Linh Nguyen; https://doi.org/10.3390/pharmaceutics 14030572 Pharmacokinetics and Pharmacodynamics of Intranasal Solid Lipid Nanoparticles and Nanostructured Lipid Carriers for Nose-to-Brain Delivery (Year: 2022).*

Kousalya Selvaraj; https://www. tandfonli ne. com/action/ showCitFormats?doi=10.1080/21691401.2017. 1420073 Nose to brain transport pathways an overview: potential of nanostructured lipid carriers in nose to brain targeting (Year: 2017).*

Sheetal Porecha Acharya; DOI 10.1007/s40005-015-0190-3 Development of phenytoin intranasal microemulsion for treatment of epilepsy (Year: 2015).*

Mukta Agrawal; https://doi.org/10.1016/j.jconrel.2020.02.020 Recent strategies and advances in the fabrication of nano lipid carriers and their application towards brain targeting (Year: 2020).*

Sreeja C. Nair et al., "Nose to Brain Delivery of Phenytoin Sodium Loaded Nano Lipid Carriers: Formulation, Drug Release, Permeation and In Vivo Pharmacokinetic Studies", Pharmaceutics 2021, 13, 1640. https://doi.org/10.3390/pharmaceutics13101640.

* cited by examiner

*Primary Examiner* — Robert A Wax
*Assistant Examiner* — Andre Mach
(74) *Attorney, Agent, or Firm* — Foley & Lardner LLP

(57) ABSTRACT

The present invention discloses a formulation comprising nano lipid carrier encapsulated active pharmaceutical ingredient suitable for rapid delivery of said active pharmaceutical ingredient to brain via intranasal olfactory route for managing acute epileptic emergency. The present invention also discloses a process for the preparation of said formulation and a method for treating acute epileptic emergency by administering therapeutically effective dose of said formulation.

6 Claims, 13 Drawing Sheets

Fig. 3A
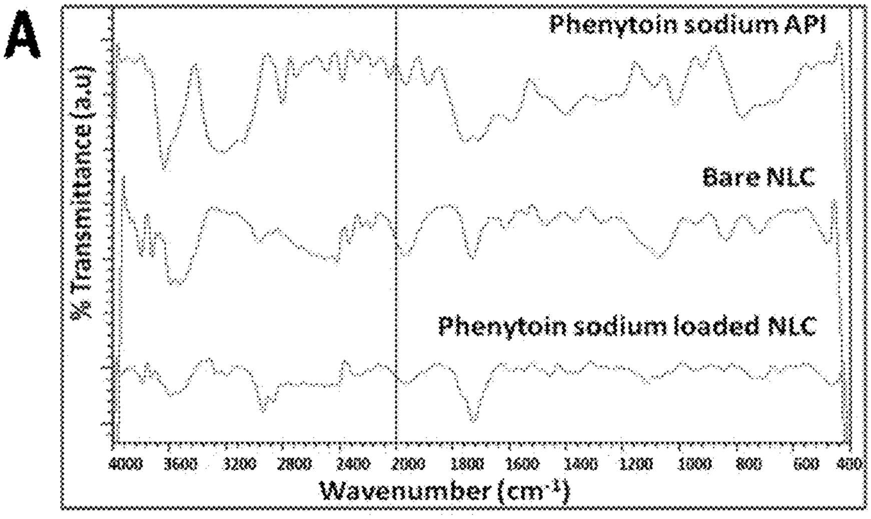
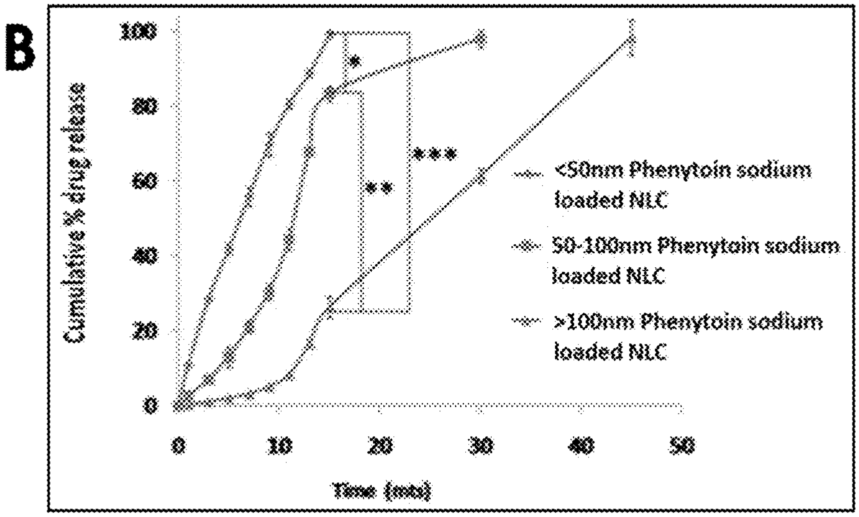
Fig. 3B

FEMALE RATS

MALE RATS

Fig. 7A
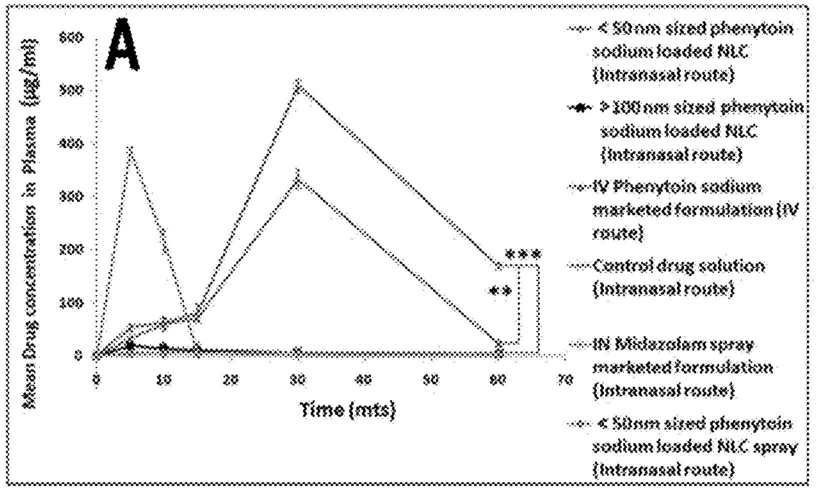
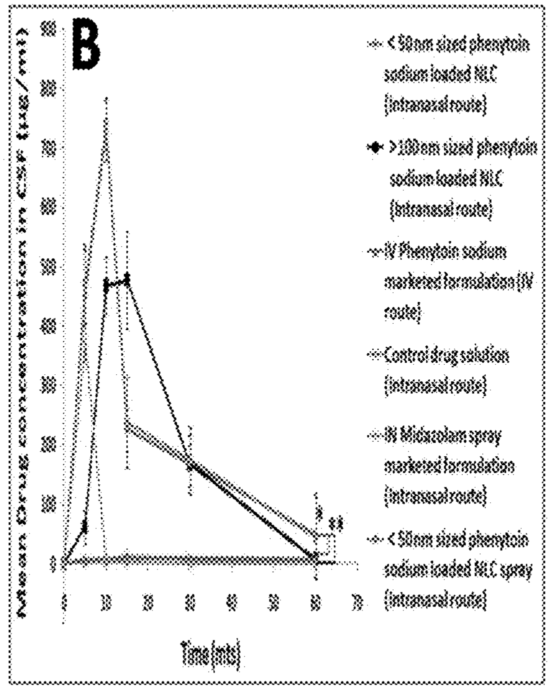
Fig. 7B
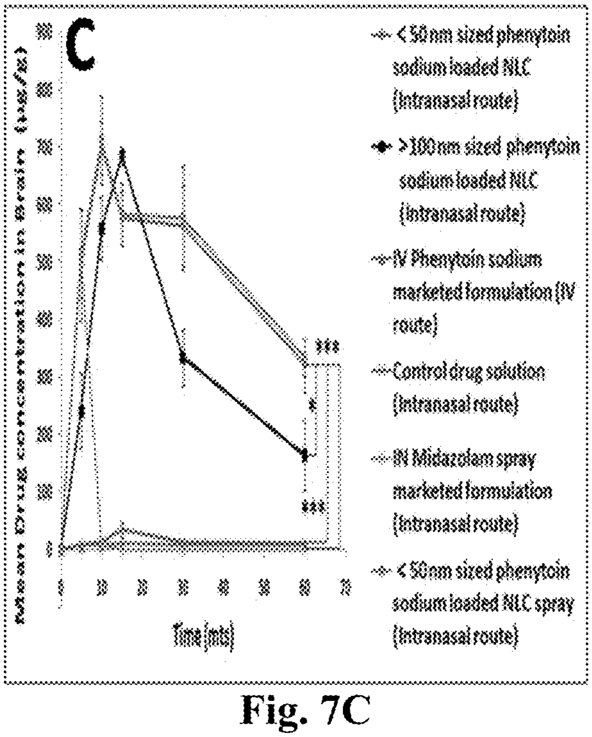
Fig. 7C

Fig. 8A
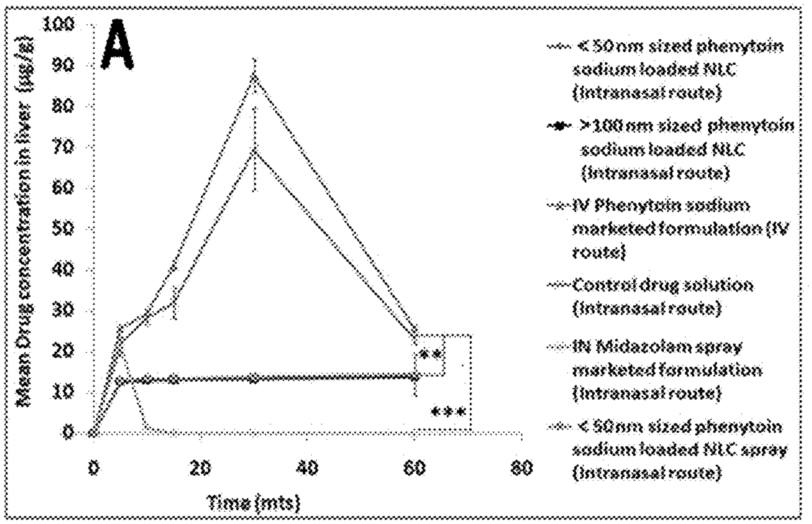
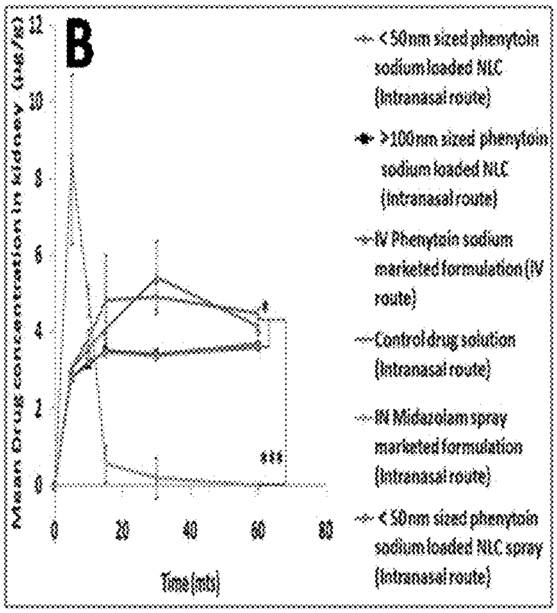
Fig. 8B
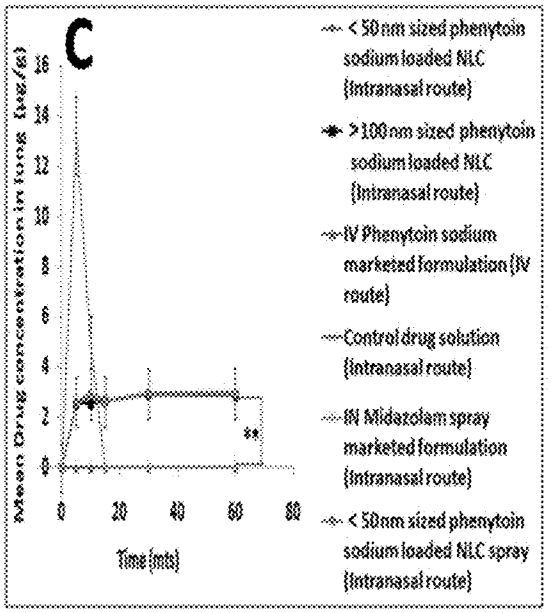
Fig. 8C

Fig. 9A
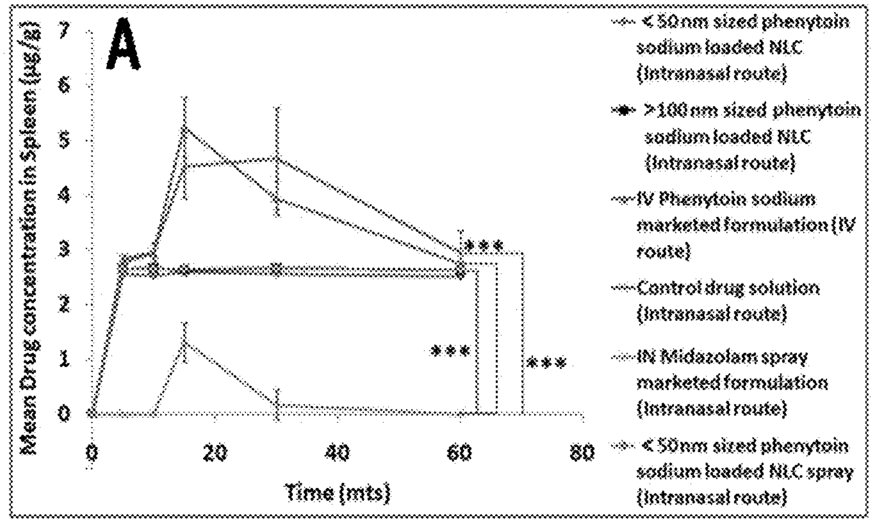
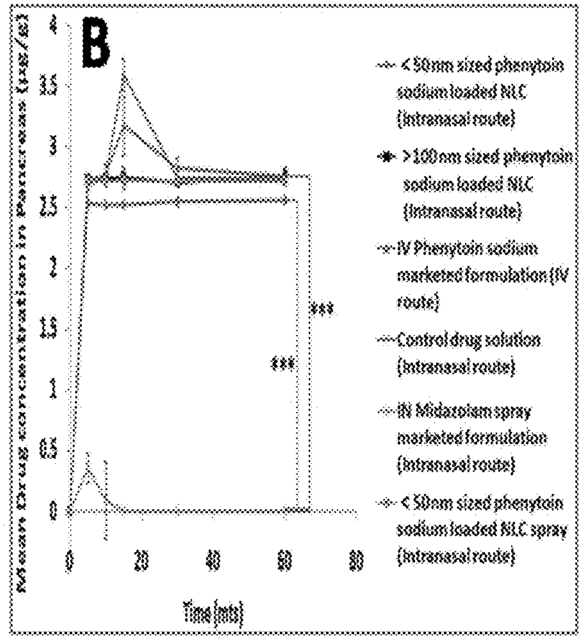
Fig. 9B
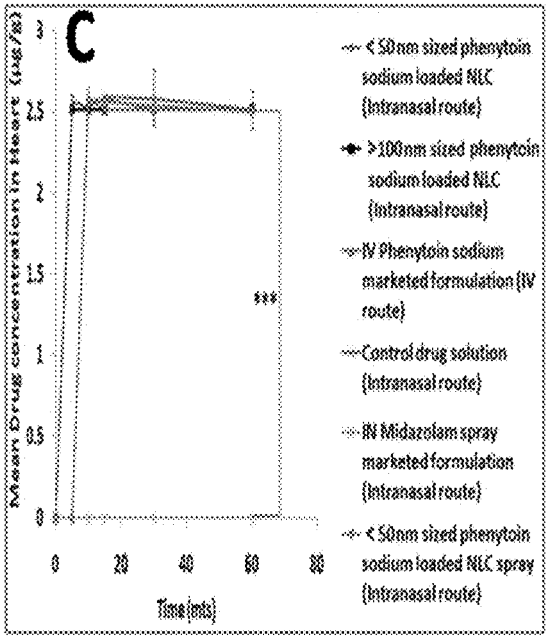
Fig. 9C

NANOLIPID CARRIER BASED FORMULATION FOR BRAIN DELIVERY THROUGH INTRANASAL ROUTE AND ITS PREPARATION PROCESS

FIELD OF THE INVENTION

The present invention pertains to the field of pharmaceutics. Particularly, the present invention discloses a formulation comprising nano lipid carrier encapsulated active pharmaceutical ingredient suitable for rapid delivery of said active pharmaceutical ingredient to brain via intranasal olfactory route for managing acute epileptic emergency. The present invention also discloses a process for the preparation of said formulation and a method for treating acute epileptic emergency by administering therapeutically effective dose of said formulation.

BACKGROUND AND DESCRIPTION OF RELATED ART

A seizure emergency, commonly known as status epilepticus is a prolonged seizure or frequently occurring seizure which needs immediate medical attention. Seizures extending for more than five minutes are treated as extremely severe and fatal ones and are called status epilepticus. Mortality and worse neurologic outcome are directly associated with the duration of seizure activity.

The complexity of blood brain barrier (BBB) & the barrier function of the brain endothelium denies the entry of therapeutic drugs into the brain. As a result, only small molecular weight, <1,000 Daltons) lipid-soluble molecules can freely cross the BBB. In addition, molecular efflux pumps, which use cellular energy to pump drugs that might cross the BBB back into the vessel lumen, decrease the ability of many prospective anti-epileptic drugs (AEDs) to reach the brain sufficiently. Even before drugs can reach the brain, factors such as systemic toxicity and macrophage phagocytosis within the reticulo-endothelial system (RES) limit the success of the drugs delivered via trans vascular route.

The IV (intravenous) benzodiazepines including lorazepam, midazolam and diazepam remain the first line therapeutic agents for the immediate treatment of status epilepticus once the patient reaches hospital. The second line therapy includes IV phenytoin sodium or fosphenytoin. The availability of benzodiazepines suitable for administration by alternative routes (other than IV and IM (intramuscular)) such as rectal, buccal and intranasal offer additional advantage, facilitating their use immediately and outside the hospital. In fact, these benzodiazepines are short acting with an elimination half-life of 1.5 hrs and so, mostly a second dose is needed after 5 minutes or need to start second line Anti-Epileptic Drugs (AED) immediately. There is an increased likelihood of fatal respiratory failure or arrest while using benzodiazepines, which increases with frequent repeated dosing.

The IV phenytoin sodium remains the second line therapeutic agent for the immediate treatment of status epilepticus. It is a well-established and cost-effective traditional drug having long biological half-life of 15-22 hrs with longer duration of action (24 hrs). It does not produce any CNS depression or sedation compared to other AEDs. The disadvantages of phenytoin sodium include fatal hypotension and arrhythmias and it is available as tablet and injections only, limiting its use outside the hospital setting in acute conditions. Due to high alkalinity of available phenytoin sodium IV injection (pH12), it may cause venous irritation and can only be given as slow intravenous push at a concentration of 50 mg/min. Even at a lower infusion rate, profound hypotension was noticed with unstable blood pressure or shock. Due to the above issues, it has slow onset of action of around 30 minutes and a large dose of 1-1.5 g (15-25 mg/kg dose) is necessary to achieve clinical effects, due to the insufficient and inadequate delivery of phenytoin sodium to the brain which ultimately results in potential peripheral toxic side effects.

Considering the afore-mentioned limitations, as well as its unpredictable non-linear pharmacokinetic profile, clinicians have started prescribing other AEDs which are costlier than phenytoin with undesirable CNS depressant effects too. Hence newer formulations are highly essential for this affordable and well-established AED to bring it back to the clinic to utilize it in acute epileptic emergencies. There is a pronounced need in the art for new mechanisms of delivering phenytoin sodium to the brain.

Hence to address these problems, novel strategies with nanotechnological approaches are aimed to make the transit easier for these agents to bypass the BBB, phagocytic and efflux mechanisms thus facilitating attainment of therapeutic concentrations in brain. In this line, a patent application describes compositions and methods related to antibodies or antibody fragments which are able to cross the blood brain barrier. Further it also discloses methods of delivering an agent to the brain of a subject, the method comprising administering to the subject a composition comprising a conjugate comprising Pritumumab and one or more agents.

Another patent application describes an invention belonging to the field of pharmaceuticals and relates to a cascade brain-targeting drug delivery system and the application thereof. The cascade brain-targeting drug delivery system comprises a first-stage target functional molecule, a second-stage target functional molecule and a drug carrier. The cascade target drug delivery system can identify the blood-brain barrier through the first-stage target functional molecule and identify a brain lesion through the second-stage target functional molecule, so as to achieve the accurate targeting purpose, and can also accurately transfer imaging molecules or drugs to the brain lesion, so as to achieve good imaging and therapeutic effects. The cascade brain-targeting drug delivery system can be applied to prepare formulations for treatment or diagnosis of brain diseases (such as brain tumors) and nervous system diseases.

Yet another patent describes an invention relating to a compound delivery device for delivering a plume derived from a propellant and a drug formulation. The drug formulation is in an intranasal dosage form in the form of powder, suspension, dispersion, or liquid. The propelled intranasal dosage form is deposited within the olfactory region of the nasal cavity. The drug deposited within the olfactory region is delivered to the brain avoiding the blood-brain-barrier. Hydrofluoroalkane propellant from a pressurized canister is channeled to a diffuser and drug-containing chamber where the intra-nasal dosage form is aerosolized. The aerosolized intra-nasal dosage form passes through a nozzle thus delivering a plume to the olfactory region of a user's nasal cavity.

One more patent provides an invention relating to a method for enhanced delivery of Bupropion by administration via the nasal route, and methods of treatment comprising intranasal administration of bupropion. This invention further provides pharmaceutical compositions comprising bupropion and/or pharmaceutically acceptable salts thereof.

However, no study has been reported relating to an intranasal nanolipid carrier (NLC) formulation of hydantoin derivative comprising but not limited to phenytoin sodium, for direct nose to brain targeting, with quick onset of action in case of seizure emergencies, which delivers the antiepileptic drug directly into the brain so as to minimize dose related side effects, thus providing a unique feature and better option for enhanced brain delivery. The present invention discloses intranasal NLC formulation of sufficient lipophilicity and particle size less than 50 nm (10 to 45 nm) which can potentially deliver the drug to the brain via extracellular pathways of olfactory cells that reaches into the olfactory bulb and CSF to reach the brain directly.

OBJECTIVES OF THE INVENTION

An objective of the invention is to provide a biocompatible non-toxic formulation of anti-epileptic drug suitable for rapid delivery of said drug to brain via intranasal olfactory route for managing acute epileptic emergency.

Another objective of the invention is to provide a process for the preparation of biocompatible non-toxic formulation of anti-epileptic drug suitable for rapid delivery of said drug to brain via intranasal olfactory route for managing acute epileptic emergency.

Yet another objective of the invention is to provide a method for treating acute epileptic emergency.

SUMMARY OF THE INVENTION

An aspect of the invention pertains to an intranasal formulation comprising a nano lipid carrier (NLC), active pharmaceutical ingredient suitable for rapid delivery of active pharmaceutical ingredient to brain directly via intranasal olfactory route for managing acute epileptic emergency, wherein the active pharmaceutical ingredient is encapsulated within the nano lipid carrier; wherein the nano lipid carrier comprises at least one solid lipid, at least one liquid lipid and a surfactant and has a particle size of less than 50 nm or 50-100 nm or 100 to 150 nm; wherein the active pharmaceutical ingredient is a hydrophobic drug selected from hydantoin derivatives.

Another aspect of the invention pertains to a process for the preparation of intranasal formulation comprising a nano lipid carrier (NLC), active pharmaceutical ingredient suitable for rapid delivery of active pharmaceutical ingredient to brain directly via intranasal olfactory route for managing acute epileptic emergency, wherein the active pharmaceutical ingredient is encapsulated within the nano lipid carrier; wherein the nano lipid carrier comprises at least one solid lipid, at least one liquid lipid and a surfactant and has a particle size of less than 50 nm or 50-100 nm or 100 to 150 nm; wherein the active pharmaceutical ingredient is a hydrophobic drug selected from hydantoin derivatives.

Yet another aspect of the invention pertains to a method for treating acute epileptic emergency by administering therapeutically effective dose of the intranasal formulation comprising a nano lipid carrier, active pharmaceutical ingredient, wherein the active pharmaceutical ingredient is encapsulated within the nano lipid carrier; wherein the nano lipid carrier comprises at least one solid lipid, at least one liquid lipid and a surfactant and has a particle size of <50 nm or 50-100 nm or 100-150 nm; wherein the active pharmaceutical ingredient is a hydrophobic drug selected from hydantoin derivative.

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 3A: Characterization of NLC by FTIR (Fourier transform infrared) analysis.

FIG. 3B: In vitro drug release study of phenytoin sodium NLCs.

FIG. 7A: Graphical representation of mean plasma, drug concentration profile following intranasal administration of phenytoin sodium NLCs, control drug solution, midazolam marketed formulation and IV administration of phenytoin sodium marketed formulation.

FIG. 7B: Graphical representation of mean CSF, drug concentration profile following intranasal administration of phenytoin sodium NLCs, control drug solution, midazolam marketed formulation and IV administration of phenytoin sodium marketed formulation.

FIG. 7C: Graphical representation of mean brain, drug concentration profile following intranasal administration of phenytoin sodium NLCs, control drug solution, midazolam marketed formulation and IV administration of phenytoin sodium marketed formulation.

FIG. 8A: Graphical representation of mean liver, drug concentration profile following intranasal administration of phenytoin sodium NLCs, control drug solution, midazolam spray marketed formulation and IV administration of phenytoin sodium marketed formulation.

FIG. 8B: Graphical representation of mean kidney drug concentration profile following intranasal administration of phenytoin sodium NLCs, control drug solution, midazolam spray marketed formulation and IV administration of phenytoin sodium marketed formulation.

FIG. 8C: Graphical representation of mean lung drug concentration profile following intranasal administration of phenytoin sodium NLCs, control drug solution, midazolam spray marketed formulation and IV administration of phenytoin sodium marketed formulation.

FIG. 9A: Graphical representation of mean spleen drug concentration profile following intranasal administration of phenytoin sodium NLCs, control drug solution, midazolam marketed formulation and IV administration of phenytoin sodium marketed formulation.

FIG. 9B: Graphical representation of mean pancreas drug concentration profile following intranasal administration of phenytoin sodium NLCs, control drug solution, midazolam marketed formulation and IV administration of phenytoin sodium marketed formulation.

FIG. 9C: Graphical representation of mean heart drug concentration profile following intranasal administration of phenytoin sodium NLCs, control drug solution, midazolam marketed formulation and IV administration of phenytoin sodium marketed formulation.

DETAILED DESCRIPTION OF THE INVENTION

Figure 1:
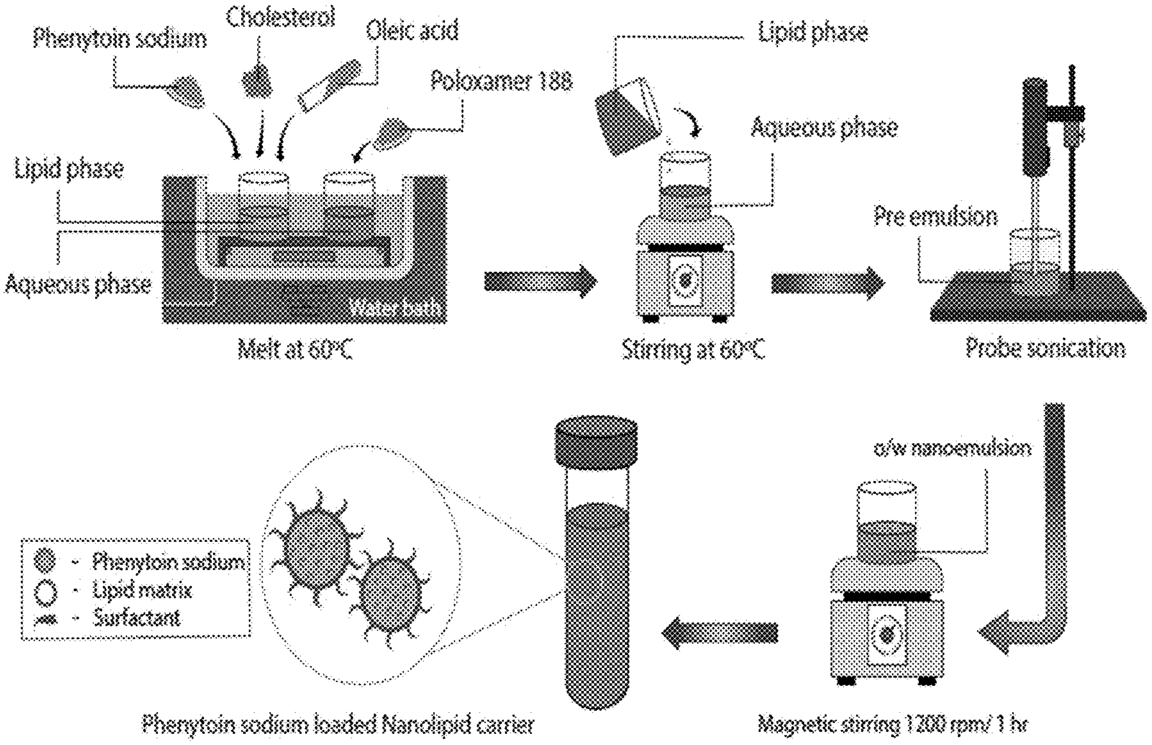
FIG. 1: Schematic representation of method of preparation of phenytoin sodium loaded NLC.
Figures 2A, 2B, 2C, 2D:
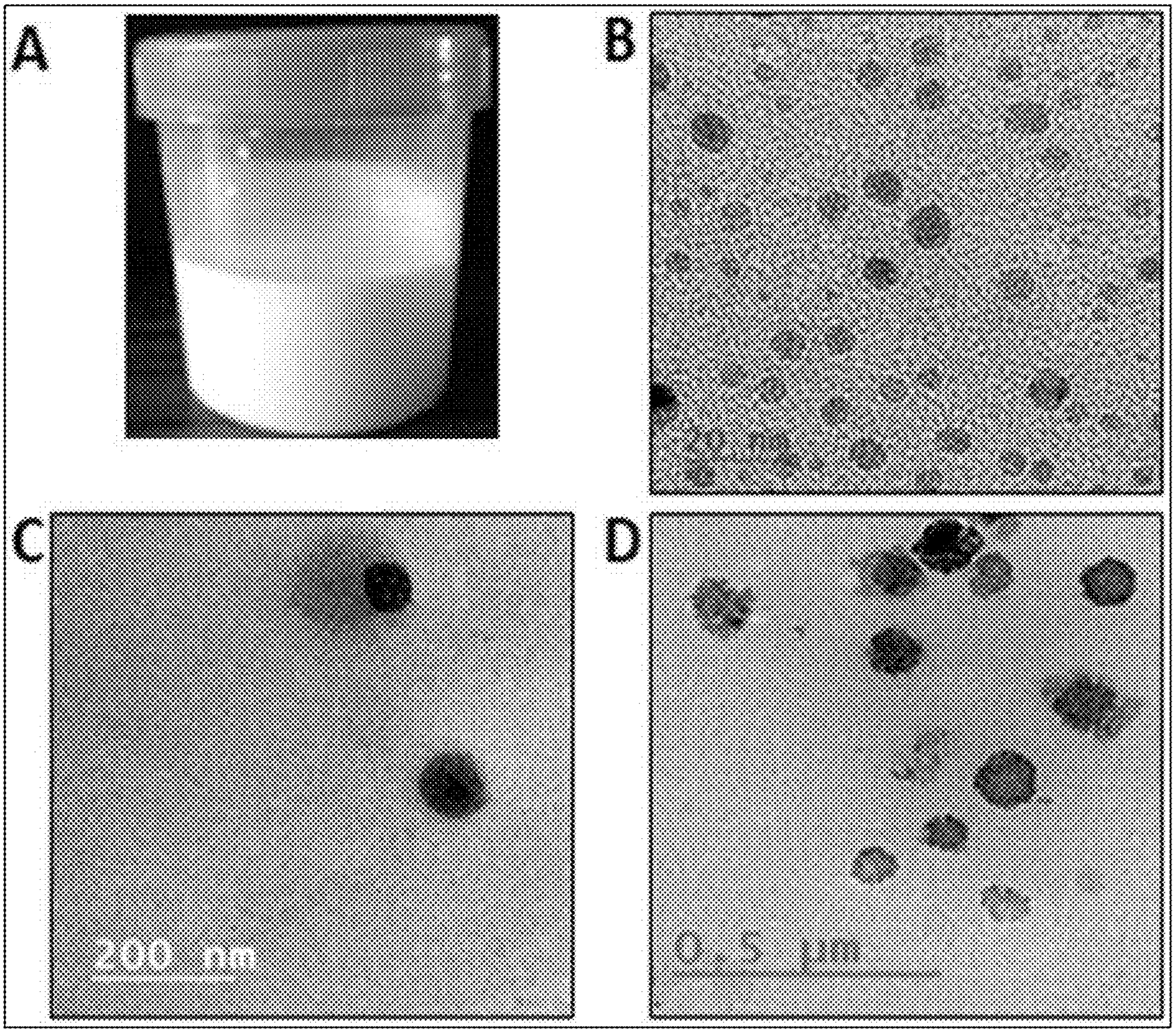
FIG. 2A: TEM (Transmission Electron Microscopy) images of <50 nm sized phenytoin sodium loaded NLC.
FIG. 2B: TEM (Transmission Electron Microscopy) images of 50-100 nm sized phenytoin sodium loaded NLC.
FIG. 2C: TEM (Transmission Electron Microscopy) images of >100 nm sized phenytoin sodium loaded NLC.
FIG. 2D: TEM (Transmission Electron Microscopy) image of 0.5 μm sized phenytoin sodium loaded NLC.
Figures 4A, 4B, 4C, 4D:
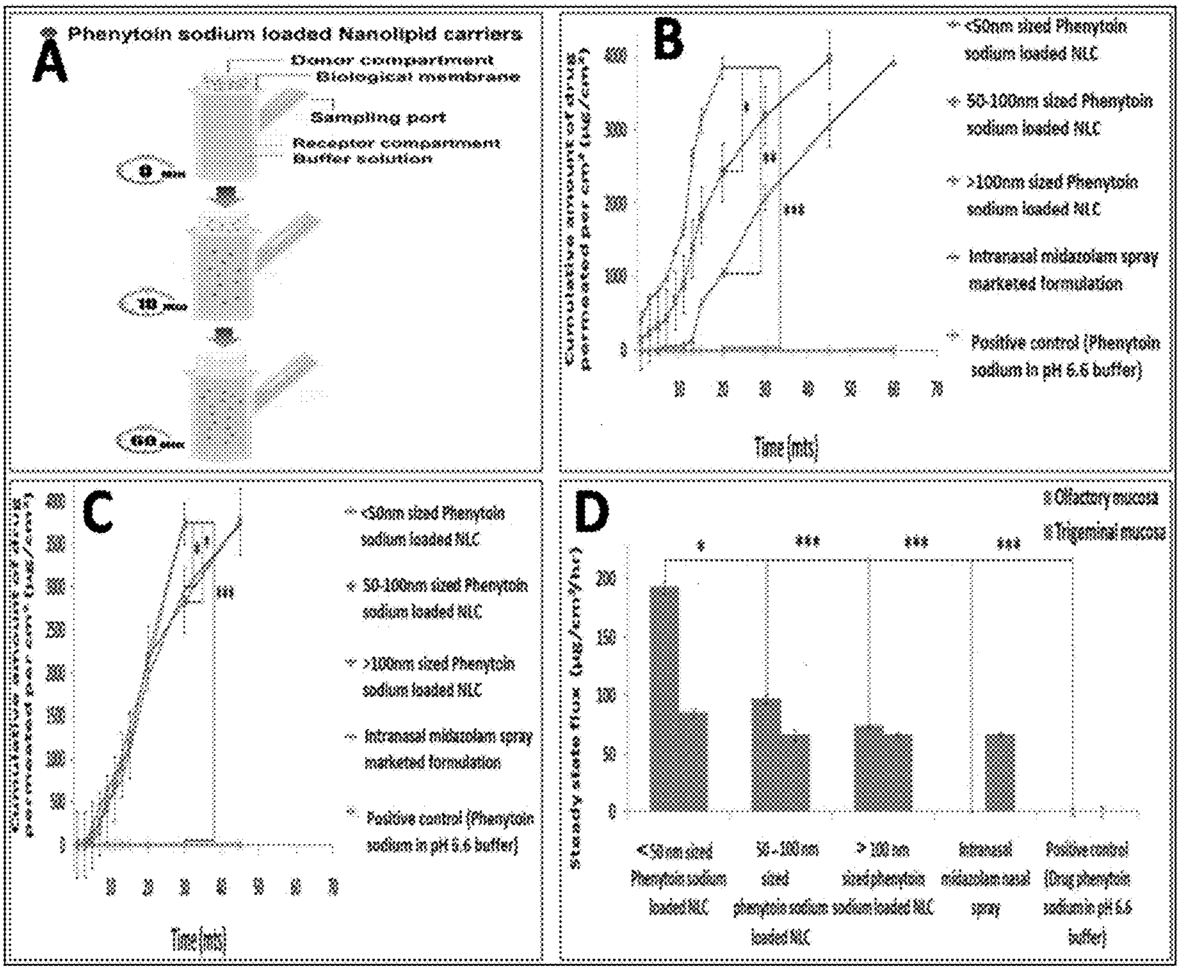
FIG. 4A: Schematic representation of ex vivo permeation study of phenytoin sodium NLCs.
FIG. 4B: Ex vivo permeation study of Phenytoin sodium NLCs using olfactory mucosa.
FIG. 4C: Ex vivo permeation study of Phenytoin sodium NLCs using trigeminal mucosa.
FIG. 4D: Steady-state flux determination of various intranasal formulations.
Figures 5A, 5B:
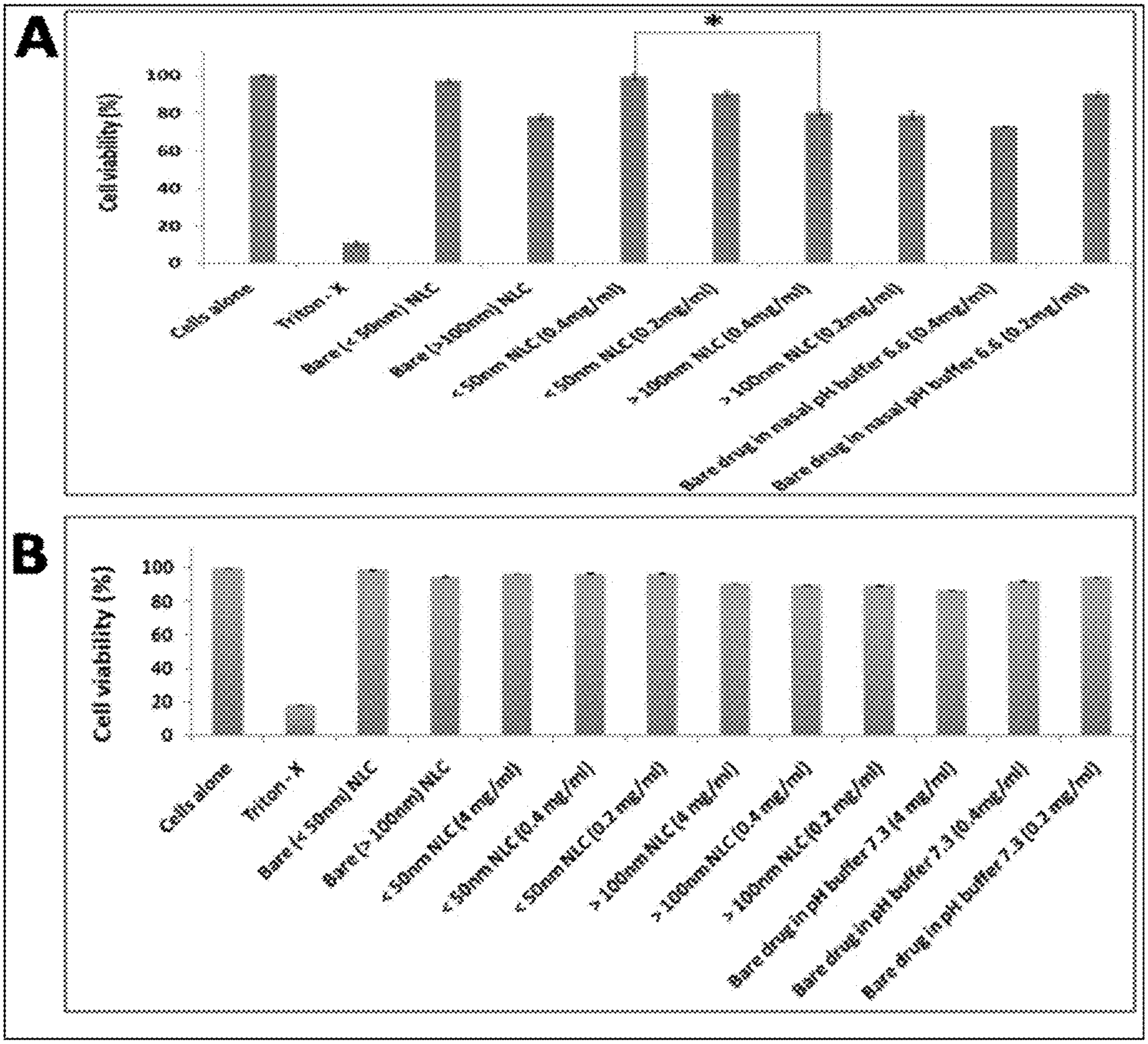
FIG. 5A: Cytocompatibility studies of the prepared phenytoin sodium loaded nano lipid carriers and bare drug in L929 cell line.
FIG. 5B: Cytocompatibility studies of the prepared phenytoin sodium loaded nano lipid carriers and bare drug in HBCEC cell line.
Figure 6A:
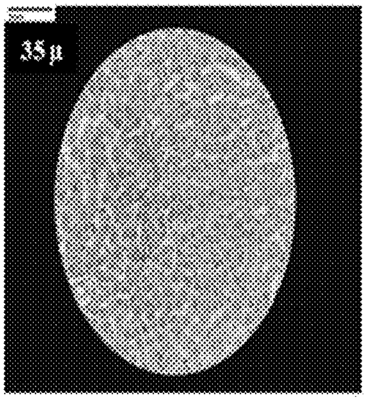
FIGS. 6A-6C: Liver histopathology images of female wistar rats treated with 500 mg/kg dose phenytoin sodium loaded NLC after acute toxicity study.
Figure 6B:
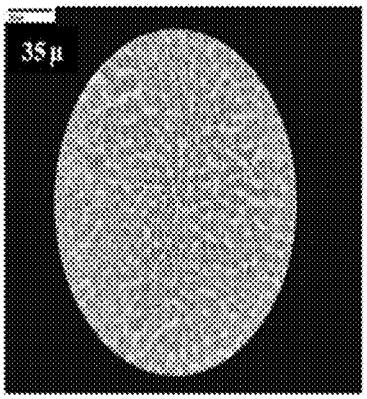
Figure 6C:
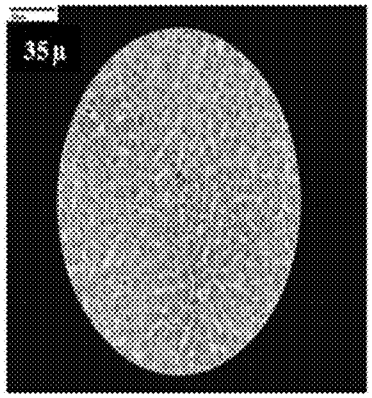
Figure 6D:
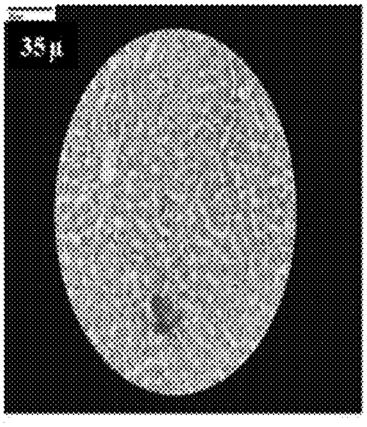
FIGS. 6D-6F: Liver histopathology images of male wistar rats treated with 500 mg/kg dose phenytoin sodium loaded NLC after acute toxicity study.
Figure 6E:
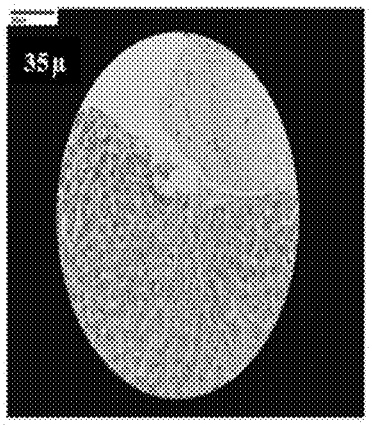
Figure 6F:
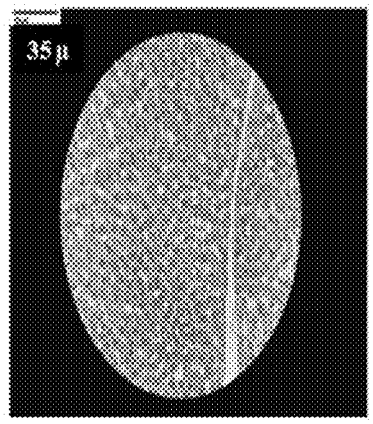
Figure 6G:
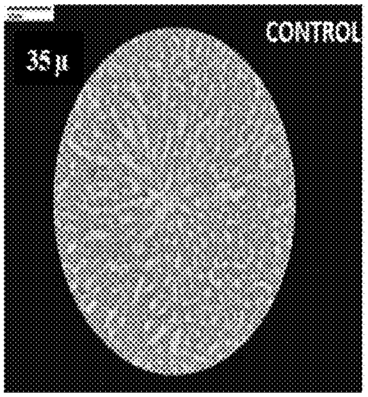
FIG. 6G: Liver histopathology images of normal control group after acute toxicity study.
Figure 10:
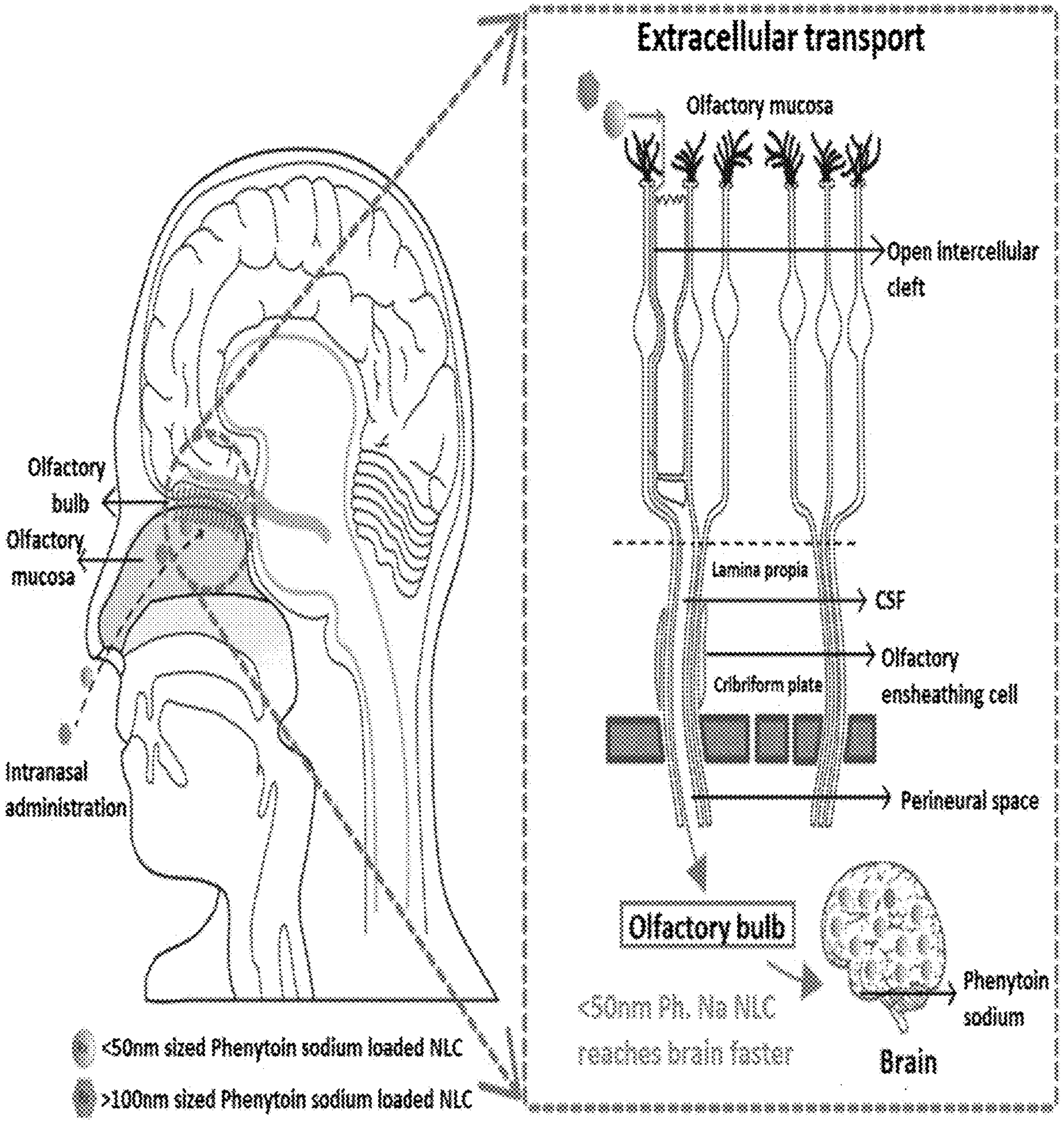
FIG. 10: Diagram showing direct nose to brain delivery of phenytoin sodium NLCs through olfactory epithelium by the extracellular perineural transport mechanism.
Figure 11:
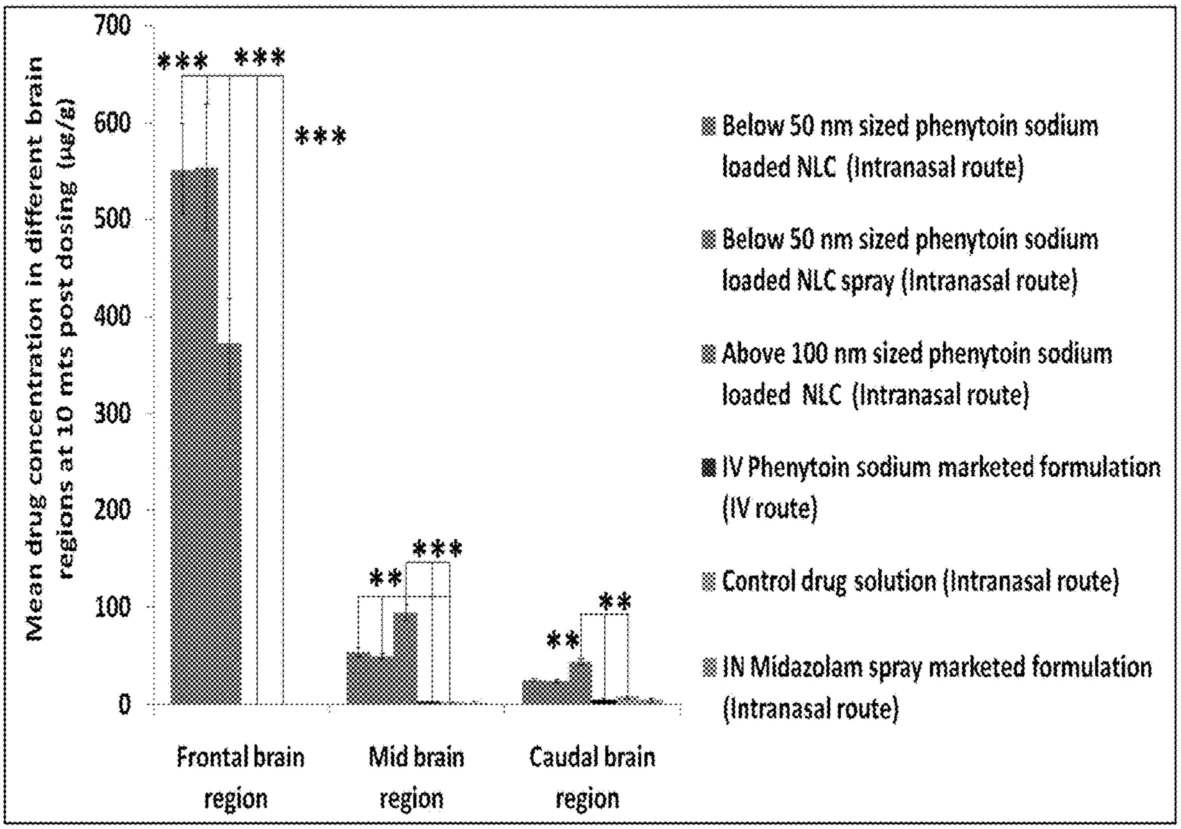
FIG. 11: Bar graph showing the mean drug concentration in different brain regions at 10 mts post dosing of various formulations.
Figure 12:
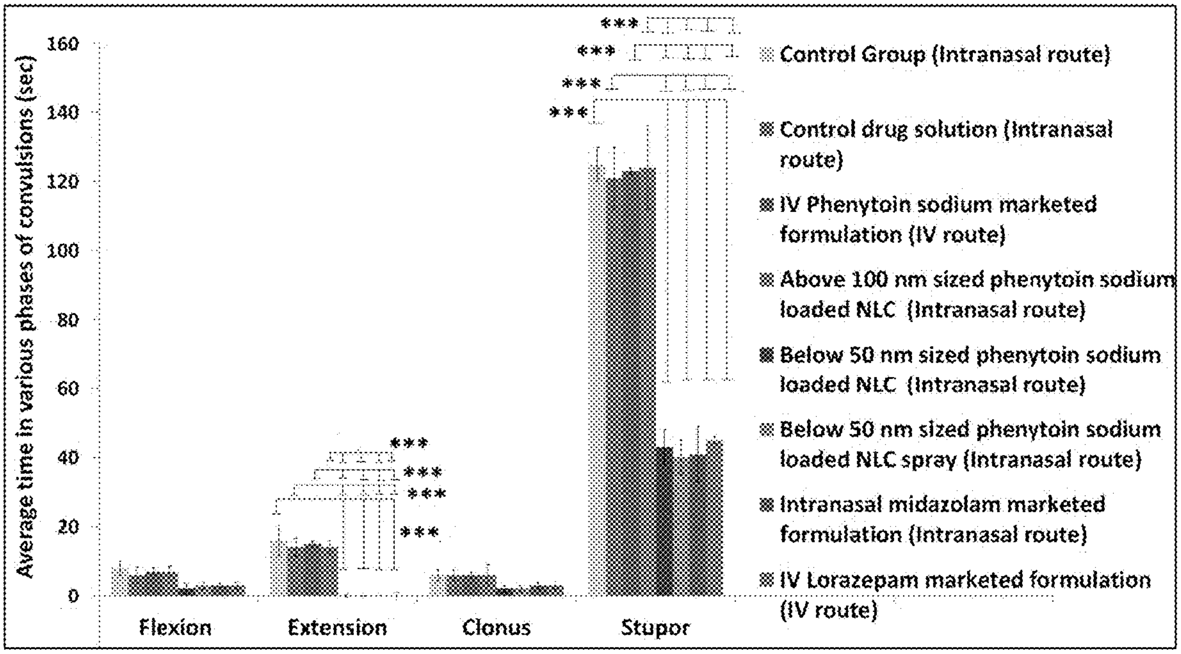
FIG. 12: Bar graph showing the in vivo anticonvulsant activity study of phenytoin sodium loaded NLCs and its comparison with marketed drug formulations and control drug solution.
Figure 13:
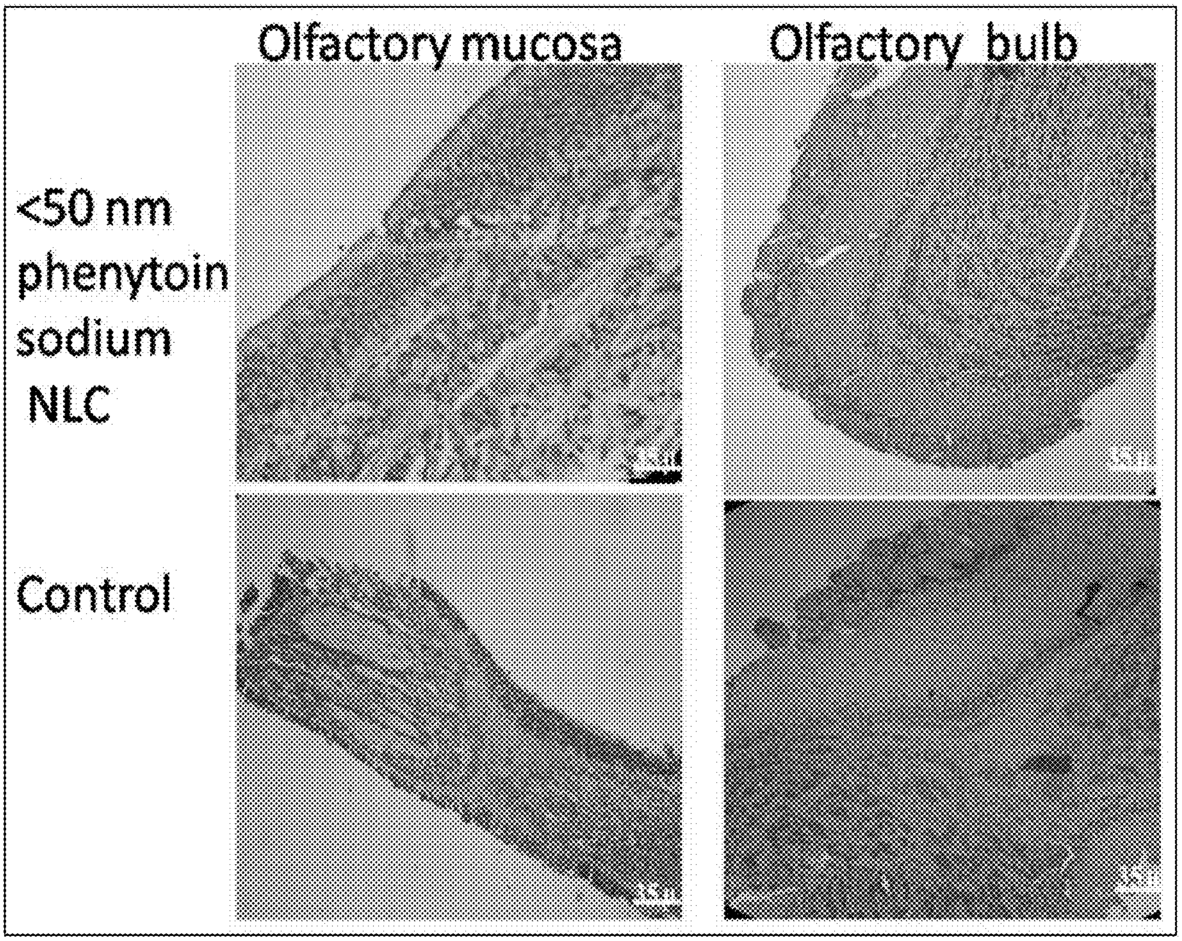
FIG. 13: Histopathology images of rat's nasal olfactory mucosa and olfactory bulb after treatment with <50 nm sized phenytoin sodium NLC as well as control drug solution.

For the purposes of the following detailed description, it is to be understood that the invention may assume various alternative variations and step sequences, except where expressly specified to the contrary. Thus, before describing the present invention in detail, it is to be understood that this invention is not limited to particularly exemplified systems or process parameters that may, of course, vary.

It is also to be understood that the terminology used herein is for the purpose of describing embodiments of the invention only and is not intended to limit the scope of the invention in any manner. The use of examples anywhere in this specification, including examples of any terms discussed herein, is illustrative only and in no way limits the scope and meaning of the invention or any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions, will control. It must be noted that, as used in this specification and the appended claims, the singular forms "a," "an" and "the" include plural referents unless the content clearly dictates otherwise. The terms "preferred" and "preferably" refer to embodiments of the invention that may afford certain benefits under certain circumstances. However, other embodiments may also be preferred under the same or other circumstances. Furthermore, the recitation of one or more preferred embodiments does not imply that other embodiments are not useful and is not intended to exclude other embodiments from the scope of the invention.

As used herein, the terms "comprising" "including" "having" "containing" "involving" and the like are to be understood to be open-ended, i.e., to mean including but not limited to.

As used herein, the phrase "therapeutically effective dose" is an amount sufficient to effect desired clinical results (i.e., achieve therapeutic efficacy). In the present case, the desired clinical result includes inhibition of seizure activity. A therapeutically effective dose can be administered in one or more administrations.

An aspect of the invention pertains to an intranasal formulation suitable for delivering active pharmaceutical ingredient to brain for managing acute epileptic emergency, comprising a nano lipid carrier, active pharmaceutical ingredient, wherein the active pharmaceutical ingredient is encapsulated within the nano lipid carrier; wherein the nano lipid carrier comprises a solid lipid, a liquid lipid and a surfactant and has a particle size of <50 nm or 50-100 nm or 100 to 150 nm; wherein the active pharmaceutical ingredient is a hydrophobic drug selected from hydantoin derivatives.

In a preferable embodiment of the intranasal formulation the particle size of nano lipid carrier encapsulated active pharmaceutical ingredient is in the range of 10 to 45 nm.

In various embodiments of the intranasal formulation, the particle size of nano lipid carrier encapsulated active pharmaceutical ingredient varies within three ranges, from 10 to 45 nm (below 50 nm), between 50 nm and 100 nm and between 100 nm to 150 nm.

In an embodiment of the intranasal formulation, wherein the nano lipid carrier having the particle size of 10-45 nm has a percentage entrapment efficiency (EE) and drug loading (DL) of 91.17±4.48% and 39.43±2.80% respectively.

In yet another embodiment of the intranasal formulation, wherein the nano lipid carrier having the particle size of 50-100 nm has a percentage entrapment efficiency (EE) and drug loading (DL) of 87.70±1.19% and 36.92±4.71% respectively.

In another embodiment of the intranasal formulation, wherein the nano lipid carrier having the particle size of 100-150 nm has a percentage entrapment efficiency (EE) and drug loading (DL) of 81.35±3.17% and 32.54±1.27% respectively.

In a specific embodiment of the intranasal formulation, the active pharmaceutical ingredient is phenytoin sodium and the amount of Phenytoin Sodium in said formulation ranges from 4 mg/ml to 10 mg/ml.

In various embodiments of the intranasal formulation, the solid lipid comprises fatty acids including but not limited to stearic acid, steroids including but not limited to cholesterol, or waxes including but not limited to cetyl palmitate or a combination thereof.

In a preferred embodiment of the intranasal formulation, the solid lipid selected is a steroid-cholesterol which is biodegradable and biocompatible in nature.

In various embodiments of the intranasal formulation the liquid lipid comprises triglycerides including but not limited to tristearin, diglycerides including but not limited to glycerol bahenate, monoglycerides including but not limited to glycerol monostearate or long chain fatty acids including but not limited to oleic acid, stearic acid or a combination thereof. Preferably, the liquid lipid used is oleic acid, which is biocompatible that forms the part of biological membrane.

In various embodiments of the intranasal formulation, the surfactant comprises poloxamers [triblock copolymers of poly (ethylene oxide) (PEO) and poly (propylene oxide) (PPO)] which is used to stabilize the lipid core.

In a specific embodiment of the intranasal formulation, the solid lipid of nano lipid carrier is cholesterol, liquid lipid of nano lipid carrier is oleic acid, both are biocompatible and forms part of biological membrane of nano lipid carrier, the surfactant of nano lipid carrier is poloxamer, which act as a permeation enhancer & membrane stabilizer which enhances the colloidal stability of the nano lipid carrier and the active pharmaceutical ingredient is phenytoin sodium.

In various embodiments of the intranasal formulation the solid lipid is present in an amount of 15 to 20% w/w, liquid lipid is present in an amount of 80 to 85% w/w, the surfactant is present in an amount of 1 to 1.5% w/v in the nano lipid carrier. The surfactant concentration affects storage stability of NLCs. Lipid nanoparticles stabilized with liquid lipid have been found to have lower particle size and higher storage stability compared to formulations with solid lipid alone.

In various embodiments, the intranasal formulation is in the form of spray or mist which can be administered as unit dose formulation to achieve the desired therapeutic dose overcoming the disadvantages of already available formulations.

In various embodiments, the intranasal formulation comprises pharmaceutically acceptable carriers or excipients which are biocompatible in nature consisting of liquid lipid comprises triglycerides including but not limited to tristearin, diglycerides including but not limited to glycerol beffenate, monoglycerides including; but not limited to glycerol monostearate or long chain fatty acids including but not limited to oleic acid, stearic acid, or a combination thereof. Preferably, the liquid lipid used is oleic acid, which is biocompatible that forms the part of biological membrane.

In an embodiment of intranasal formulation designed to control acute seizures, the in vitro drug release study demonstrated an immediate drug release from nano lipid carrier encapsulated phenytoin sodium of particle size ranging from 10 to 45 nm size, within 15 minutes. This immediate drug release is highly essential for treating acute epileptic seizure.

In an embodiment of intranasal formulation, ex vivo permeation studies indicated faster and greater permeation of phenytoin sodium from nano lipid carrier encapsulated phenytoin sodium of particle size ranging from 10 to 45 nm size through olfactory epithelium as compared to other sized nano lipid carrier encapsulated phenytoin sodium (50-100 nm sized and 100-150 nm sized NLC) and intranasal control drug solution with a higher flux value.

In various embodiments of intranasal formulation, different sized nano lipid carrier encapsulated phenytoin sodium showed good biocompatibility with both L929 and HBCE cells.

In various embodiments of intranasal formulation, nano lipid carrier encapsulated phenytoin sodium is found non-toxic up to 250 mg/kg dose.

Another aspect of the invention pertains to a method for making the intranasal formulation comprising a nano lipid carrier, active pharmaceutical ingredient, wherein the active pharmaceutical ingredient is encapsulated within the nano lipid carrier; wherein the nano lipid carrier comprises a solid lipid, a liquid lipid and a surfactant and has a particle size of <50 nm or 50-100 nm or 100-150 nm; wherein the active pharmaceutical ingredient is a hydrophobic drug selected from hydantoin derivatives comprising the steps of melt emulsification and ultrasonication; wherein a) melt emulsification comprises
   - addition of active pharmaceutical ingredient to preheated mixture of lipids comprising cholesterol and oleic acid, which is maintained at 55-60° C. to form oil phase;
   - emulsification of the oil phase with preheated aqueous phase containing 1%-1.5% w/v of poloxamer188 in deionized water at 55-60° C., which is magnetically stirred at 1800-2000 rpm for 20-25 min to form pre-emulsion;

b) ultrasonication of pre-emulsion to form oil in water nano emulsion; wherein the ultrasonication parameters such as duration of sonication, amplitude of sonication is altered to obtain different sized particles of nano lipid carrier of intranasal formulation.

In various embodiments of the method, through optimizing the time of the probe sonication at common amplitude, the desired sized nano lipid carrier is produced. Two important factors influencing the size of NLC are the amplitude and duration of probe sonication. It was found that the particle size of NLCs decreases with increase in the duration of probe sonication. The sonication duration is 15 min at 30% amplitude for a cycle of 8 s on and 2 s off for preparing >100 nm sized nano lipid carrier encapsulated active pharmaceutical ingredient; whereas the sonication duration is 20 min at 30% amplitude for a cycle of 8 s on and 2 s off for preparing 50-100 nm sized nano lipid carrier encapsulated active pharmaceutical ingredient, and it was 25 min at 40% amplitude for a cycle of 8 s on and 2 s off for formulating optimized <50 nm sized nano lipid carrier encapsulated active pharmaceutical ingredient.

In a specific embodiment of the method, the active pharmaceutical ingredient is phenytoin sodium.

Yet another aspect of the invention pertains to a method of treating acute epileptic emergencies by administering therapeutically effective dose of intra nasal formulation comprising a nano lipid carrier, active pharmaceutical ingredient, wherein the active pharmaceutical ingredient is encapsulated within the nano lipid carrier; wherein the nano lipid carrier comprises a solid lipid, a liquid lipid and a surfactant and has a particle size of <50 nm or 50-100 nm or 100-150 nm; wherein the active pharmaceutical ingredient is a hydrophobic drug selected from hydantoin derivatives.

In an embodiment of the method of treatment, the active pharmaceutical ingredient is phenytoin sodium wherein the therapeutically effective dose ranges from 4 mg/kg to 10 mg/kg.

In a specific embodiment of the method of treatment of acute seizures, the method involves administration of therapeutically effective amount of intranasal formulation comprising nano lipid carrier encapsulated active pharmaceutical ingredient, wherein the particle size of nano lipid carrier encapsulated active pharmaceutical ingredient is in the range of 10 nm to 45 nm through olfactory pathway, wherein the active pharmaceutical ingredient is phenytoin sodium.

In an embodiment of the method of administration of therapeutically effective amount of intranasal formulation comprising nano lipid carrier encapsulated phenytoin sodium, obtained brain drug concentration of <50 nm sized phenytoin sodium NLC is around 50 times higher than brain drug concentrations obtained with administration of IV Phenytoin sodium and control drug solution treated groups, indicating rapid and direct brain drug delivery via nasal olfactory epithelium. However, the obtained liver drug concentration <50 nm sized phenytoin sodium NLC is almost ten times less than the liver drug concentrations obtained with IV Phenytoin sodium and with control drug solution. The NLC, comprising a lipid nanoparticle composition with smallest particle size (<50 nm) and sufficient lipophilicity, can deliver an effective amount of drug phenytoin sodium directly to the brain through intranasal olfactory epithelium of the nasal mucosa into olfactory bulb and CSF by extracellular-perineural convection mediated bulk flow mechanism, so as to get a rapid onset of action to provide a protective effect on brain cells against acute epileptic seizure. Particularly, the <50 nm sized Phenytoin sodium loaded NLCs (4 mg/kg dose) have another important attribute in which the dose of phenytoin sodium can be reduced by almost 20 times compared to the clinically used parenteral dose in treating acute epileptic seizures.

EXAMPLES

Materials and Methods

Phenytoin sodium API was purchased from Sigma Aldrich, St. Louis, MO, USA, and was used as received. Oleic acid was purchased from Loba Chemie (Mumbai, India). Cholesterol A.R and Pluronic-F-188 (Poloxamer) were procured from Nice Chemicals (Kochi, India). Dialysis membrane (12,000-14,000 Dalton) was from Sigma Aldrich (Bangalore, India). Fibroblast (L929) cells were purchased from National Center for Cell Sciences, Pune, India, and Human Brain Capillary Endothelial Cells (HBCEC)[ATCC-CRL-3245] were received from LGC Promochem India Pvt. Ltd. (Bangalore, India). Ethanol, acetone, potassium di hydrogen ortho phosphate, ortho phosphoric acid, diethyl ether, high pressure liquid chromatography (HPLC) grade methanol, acetone and acetonitrile were purchased from Merck Chemical Company, Mumbai, India.

Female Wistar rats (150 to 250 g weight) were used for the in vivo studies. Wistar rats are obtained from Central Lab Animal Facility, Department of Veterinary Medicine, Amrita Institute of Medical Sciences, Kochi, Kerala, India (CPCSEA Reg no. 527/02/A/CPC SEA dt 21 Jan. 2002 and renewal no. 527/PO/ReRcBi-S/ReRc-L/02/CPCSEA dt 06/05/2022). The animal experimental procedures were initiated after receiving approval from Institutional Animal Ethics Committee (IAEC), Amrita Institute of Medical Sciences, Kochi, Kerala, India (Institutional Approval No.: IAEC/2018/2/12 and IAEC/2018/2/12). The guidelines of animal handling and experimentation as per the Committee for the Purpose of Control and Supervision of Experiments on Animals (CPCSEA) in India have been followed.

Example 1: Preparation of Phenytoin Sodium (PS) Loaded NLCs

In an embodiment, Phenytoin sodium loaded NLCs were prepared by melt emulsification followed by ultra-sonication method using cholesterol as solid lipid, oleic acid as liquid lipid and poloxamer 188 as the polymer. To the preheated mixture of lipids, i.e., cholesterol and oleic acid, phenytoin sodium was added and maintained at 60° C. in a water bath. The oil phase was slowly added to a preheated aqueous phase containing 1% w/v of poloxamer188 in deionized water at 60° C. and magnetically stirred at 2000 rpm for 20 min. The obtained pre-emulsion was then ultrasonicated by using a probe sonicator (Sonics/CV18/2014) to produce an o/w nano emulsion. The probe sonication parameters were different (sonicating time was 15 min at 30% amplitude for a cycle of 8 s on and 2 s off for preparing >100 nm sized phenytoin sodium NLC; similarly, 20 min at 30% amplitude for a cycle of 8 s on and 2 s off for preparing 50-100 nm sized phenytoin sodium NLC, and it was 25 min at 40% amplitude for a cycle of 8 s on and 2 s off for formulating optimized <50 nm sized phenytoin sodium NLCs) for different sized phenytoin sodium NLCs. Finally, o/w nano emulsion obtained was cooled down to room temperature while stirring at 1200 rpm for about 1 h in a magnetic stirrer. The obtained NLCs were filtrated through a 0.45 μm membrane filter to remove the unincorporated PS aggregates. The resulting NLCs were finally washed three times with purified water. Three different nanosized phenytoin sodium loaded NLCs (<50 nm, between 50 & 100 nm and >100 nm) were obtained to reveal the effect of particle size on intranasal olfactory epithelial uptake and was further characterized.

Example 2: Characterization of Phenytoin Sodium (PS) Loaded NLCs

The average particle size of NLC was 32.59±3.42 nm (PDI-0.289), 80.0±2.45 nm (PDI-0.256) and 124.56±3.11 nm (PDI-0.303) for the 3 different sized phenytoin sodium loaded NLCs. The PDI values obtained are found below 0.35 which indicates the uniformity of particle size. All the NLCs showed a negatively charged zeta potential (−16.5±0.12 to −28.6 mV±1.87) due to the influence of negatively charged phospholipids which impart negative charge to the particle.

Cryo-TEM images revealed that the particles have spherical morphology and size was in correlation with DLS results. The percentage entrapment efficiency of the drug in the NLC was taken into account by homogenizing the prepared different sized drug-loaded NLCs using 10 mL methanol for 2 h followed by centrifugation performed in a high-speed refrigerated centrifuge (HERMLE/232HK/2014) at 15,000 rpm for 20 min at 6° C. The supernatant obtained after centrifugation was quantified by using the validated HPLC technique (LC 2010A HT SHIMADZU) at 220 nm. The total amount of drug entrapped into the NLC system can be directly quantified.

% Entrapment Efficiency=(Amount of drug entrapped/Amount of drug taken initially)×100.

For the determination of the LE, dry weight of the lyophilized form of NLC (total carrier system) was measured, and % loading efficiency (Drug Loading) was calculated as the following:

% Loading Efficiency=(Amount of drug entrapped/Total weight of NLC)×100.

The average percentage entrapment efficiency (EE) and drug loading (DL) were found to be 91.17±4.48% and 39.43±2.80% respectively for <50 nm sized phenytoin sodium loaded NLC; 87.70±1.19% and 36.92±4.71% respectively for 50-100 nm sized NLC and 81.35±3.17% and 32.54±1.27% respectively for >100 nm sized phenytoin sodium loaded NLCs.

Example 3: In Vitro Drug Release Study

The in vitro drug release study was performed using dialysis membrane technique. All the experiments were performed in triplicate. The results showed an immediate drug release of 99.19±1.07% for <50 nm sized NLCs whereas 83.27±2.01% drug release for NLCs having 50-100 nm size and 26.38±2.93% release for >100 nm sized NLCs at the end of 15 min. A complete drug release was observed within 15 min for <50 nm sized NLCs, which is highly essential for acute seizure control in epilepsy. The obtained in vitro release data of phenytoin sodium loaded NLCs were fitted to different kinetic models. The coefficient of regression (R 2 value) of different kinetic models indicates that the drug release follows zero-order kinetics, which is better fitted with the Korsmeyerpeppas model with n value more than 1 indicating that the drug release mechanism follows non-fickan transport.

Example 4: Ex Vivo Permeation Study

The ex vivo permeation comparison study using Franz diffusion cells was carried out for 1 h for 100 nm sized phenytoin sodium loaded NLCs, control drug solution (drug in pH 6.6 buffer) and intranasal midazolam spray marketed formulation using freshly excised bovine nasal mucosa by separating the upper olfactory epithelium and lower trigeminal epithelium. The cumulative olfactory permeation through <50 nm sized phenytoin sodium NLC was found to be 3843.16 $\mu g/cm^2$ at the end of 20 min which showed a size dependent faster permeation compared to other formulations, ie, from 50-100 nm sized NLC, it was found to be 3962.56 $\mu g/cm^2$ in 45 min; from >100 nm sized NLC, it was 3929.34 $\mu g/cm^2$ in 60 min; from control drug solution it was 1.09 $\mu g/cm^2$ in 60 min and no drug permeation from intranasal midazolam spray marketed formulation was seen at the end of 60 min. Similarly, the cumulative trigeminal mucosal permeation from <50 nm sized NLC was found to be 3775.12 $\mu g/cm^2$ at the end of 45 min which also showed a faster permeation compared to other formulations. From 50-100 nm sized NLC, it was found to be 3769.66 $\mu g/cm^2$; from >100 nm sized NLC it was 3752.76 $\mu g/cm^2$; from intranasal midazolam formulation it was 3732.04 $\mu g/cm^2$ and from control drug solution it was 5.68 $\mu g/cm^2$. The steady state flux value was also found to be higher for <50 nm phenytoin sodium NLC through olfactory and trigeminal mucosa compared to control drug solution and other formulations which was found to be statistically significant Example 5: In Vitro Cytocompatibility Studies by MTT Assay In vitro cytocompatibility studies of different formulations were done on L929 fibroblast cells as well as HBCEC cell lines by MTT assay. The obtained results confirmed the non-toxic nature of NLC. All the NLCs showed a cell viability of 75-99% for L929 cells and 85-99% for HBCEC cell lines, respectively after 24 h incubation. The results indicated that prepared NLCs are biocompatible.

Example 6: In Vivo Acute Toxicity Study of Phenytoin Sodium Loaded NLCs and its Comparison with Vehicle Control To identify the toxic effects of the developed intranasal formulation, an acute toxicity study was carried out on experimental animals by administering it as a single high dose of intranasal formulation. The toxicity studies were carried out as per OECD guidelines 2009, Test No. 403: Acute Inhalation Toxicity Studies (Testing of chemicals). Three consecutively high doses i.e., 100 mg/kg, 250 mg/kg and 500 mg/kg dose of phenytoin sodium loaded NLCs were administered and thereafter observed the animals for 14 days to ensure the safety of the developed IN formulation. These doses were selected based on the LD50 value of IV phenytoin sodium injection. In vivo acute toxicity study on 50 wistar rats (both male and female) revealed that NLC formulation is non-toxic up to a dose of 250 mg/kg of Phenytoin sodium but showed liver toxicity at a dose of 500 mg/kg when administered via intranasal route.

Example 7: In Vivo Pharmacokinetic and Biodistribution Studies of Phenytoin Sodium NLCs in Wistar Rats Female Wistar rats of 8 to 12 weeks age (200-250 g body weight) were used for in vivo pharmacokinetic study. All animal experiments were performed after receiving approval from the Institutional Animal Ethics Committee (IAEC), Amrita Institute of Medical Sciences, Kochi, Kerala, India (IAEC Ref. No. IAEC/2018/2/12), and all the guidelines of animal handling and experimentation were strictly followed. The study comprised of 7 groups consisting of 200 rats; each treatment group had 30 rats for a total 5 set time intervals for a total 1 h. Before drug administration, the animal was anaesthetized using 5% isoflurane in an anaesthesia chamber for not less than 1 min. For nose to brain intranasal administration in rats, volumes equivalent to 100 μL each of saline solution, <50 nm sized phenytoin sodium NLCs, >100 nm sized phenytoin sodium NLCs, control drug solution and 160 μL of intranasal midazolam marketed formulation, each containing 800 drug were instilled into the nares towards the roof of the nasal cavity targeting the olfactory mucosa region. The rats were held from the back, in a slanted position, during intranasal administration and thereafter for two minutes. For comparison, the sixth group was injected with 16 μL of intravenous (i.v.) phenytoin marketed formulation containing 800 μg of drug through the tail vein. At 5, 10, 15, 30 and 60 min, the respective rats were euthanized by keeping them in a carbon dioxide inhalation chamber with a flow rate of 3 L/min for 5 min. The in vivo pharmacokinetic study showed that higher drug concentration was seen in CSF (Cerebro spinal fluid) within 5 minutes of intranasal administration of <50 nm sized phenytoin sodium NLCs than intranasal control drug solution and marketed phenytoin sodium IV formulation and is comparable with that of intranasal midazolam spray marketed formulation. In contrast, lower drug concentration was observed in plasma after 5 min of intranasal administration of optimized <50 nm NLC formulation compared to control drug solution and marketed phenytoin sodium IV formulation. It indicates that there is minimal systemic absorption of drug-loaded NLCs administered via the intranasal route confirming that uptake is not through the systemic pathway but through the olfactory epithelial perineural pathway.

The in vivo brain biodistribution study revealed higher drug concentration in brain within 5 minutes of intranasal administration of <50 nm phenytoin sodium NLC as well as spray formulation compared to intranasal control drug solution and marketed phenytoin sodium IV formulation. This indicates a direct and rapid nose to brain drug transport of NLC through olfactory epithelium which is particle size as well as lipophilicity mediated.

The findings of drug retention study in major peripheral organs confirmed that administering phenytoin sodium as smaller sized (<50 nm) intranasal nanolipid carriers considerably reduces phenytoin distribution in peripheral tissues compared to intranasal control drug solution as well as IV phenytoin sodium marketed formulation which is highly beneficial in a clinical set up.

Example 8: In Vivo Biodistribution Study of Phenytoin Sodium Loaded NLCs into Specific Regions of Interest of Brain and its Comparison with Marketed Drug Formulations and Control Drug Solution The in vivo biodistribution of the drug into specific regions of interest of the brain, expressed as the temporal gradient of drug, (ie, maximum brain drug concentration with respect to time) was determined at 10 minutes. The result of spatial gradient study revealed that at ten-minute post-dosing of intranasal administration of Phenytoin sodium-NLC (<50 nm), phenytoin concentration exceeded in the rostral brain regions, mainly in the olfactory bulb and frontal cortex than that of the caudal brain regions, which includes caudal cortex and cerebellum, From this, it is confirmed that phenytoin is targeted to the brain via local pathways through the rostral brain region.

Example 9: In Vivo Assessment of Anticonvulsant Activity of Phenytoin Sodium Loaded NLCs and its Comparison with Marketed Drug Formulations and Control Drug Solution In the present study, anticonvulsant activity of phenytoin sodium NLCs was evaluated by using well-established model namely, Maximal electroshock induced seizure (MES) model in female wistar rats. The result of the in vivo anticonvulsant study revealed that phenytoin sodium administered via intranasal olfactory epithelial route totally abolished MES induced tonic extension phase at 5-minute post dosing of NLC as well as its spray formulations (4 mg/kg dose) which is comparable with that of intranasal midazolam and IV lorazepam marketed formulation treated groups. The same effect was obtained for the IV phenytoin sodium marketed formulation as well as intranasal control drug solution at 30-minute post dosing of formulation. The above results confirm a faster onset of drug action from <50 nm NLCs as well as from intranasal midazolam and IV lorazepam marketed formulation compared to IV phenytoin sodium marketed formulation and intranasal control drug solution.

Example 10: In Vivo Nasal Toxicity Study

The local toxic effect of the optimized NLC formulation i.e., <50 nm sized phenytoin sodium NLC was evaluated on both olfactory mucosa and olfactory bulb of wistar rats and was compared with that of normal control group. The results of the nasal histopathological studies indicated that there is no toxic impact on the microscopic structure of olfactory mucosa and olfactory bulb, as the surface epithelium lining and the granular cellular structure of the nasal mucosa and olfactory bulb were found completely intact indicating that the developed NLC formulation is safe for intranasal administration.

To summarize, the biocompatible Phenytoin sodium loaded NLCs of three different sizes (<50 nm, 50-100 nm and >100 nm) were prepared by melt emulsification method and characterized. The ideal NLC formulation was selected based on the desired particle size, DL and EE which are the key characteristics of NLC formulations for nose to brain delivery. The in vitro drug release profile indicated a complete drug release within 15 min for <50 nm sized NLCs compared to bigger sized NLCs. This immediate drug release is highly essential for the treatment of acute epileptic seizure. Further ex vivo permeation study demonstrated a higher permeation of drug through nasal olfactory epithelium from <50 nm sized phenytoin sodium NLC with enhanced flux value compared to other NLCs as well as the control drug solution. Further, in vivo pharmacokinetic study done using wistar rats showed higher drug accumulation in the CSF and brain tissues compared to other organs within 5 minutes for the <50 nm phenytoin sodium NLC administered via an intranasal olfactory route, indicating direct and rapid nose to brain drug transport through olfactory epithelium. The <50 nm sized phenytoin sodium NLCs also showed lower biodistribution in the peripheral tissues over a period of 60 minutes which is beneficial in a clinical set up. The results of in vivo biodistribution study in specific regions of interest of brain confirmed that phenytoin is targeted to the brain via local pathways through the rostral brain region. In addition, intranasal olfactory administration of <50 nm sized NLCs of phenytoin sodium provided a better protection against IVIES seizure. Hence it is concluded that <50 nm sized phenytoin sodium loaded NLCs could be an efficient carrier for the delivery of phenytoin sodium to treat acute epileptic seizure via the intranasal route. The study also revealed that the <50 nm sized phenytoin sodium NLC administered via the intranasal olfactory route is a safe and viable alternative for IV phenytoin sodium delivery.

Advantages

The intranasal formulation comprising nano lipid carrier encapsulated phenytoin sodium facilitates rapid and enhanced delivery of phenytoin sodium directly to brain favoring direct nose to brain drug transport through olfactory epithelial pathway, thus enabling faster onset of drug action. Lesser amount of drug is sufficient to achieve the intended beneficial anti-convulsant effect (arrest of acute epileptic seizures) when drug is administered via said intranasal formulation when compared to the amount of drug infused via existing Intra venous phenytoin sodium marketed formulation and intranasal control drug solution. Reduction in the effective dose results in reduced dose related peripheral toxic side effects. Additionally, the intranasal formulation is non-toxic, biocompatible, and more efficacious. Collectively, these attributes are advantageous in the treatment of acute epileptic seizure.

REFERENCES

US2021/0269513A1
CN 102552105A
U.S. Pat. No. 9,550,036B2
U.S. Pat. No. 6,150,420A

We claim:

1. An intranasal formulation, comprising a nano lipid carrier, and an active pharmaceutical ingredient, wherein the active pharmaceutical ingredient is encapsulated within the nano lipid carrier; wherein the nano lipid carrier comprises cholesterol, oleic acid and poloxamer 188 and has a particle size in a range from 25 nm to 40 nm; wherein the active pharmaceutical ingredient is phenytoin sodium, wherein the cholesterol is present in an amount of 15 to 20% w/w, the oleic acid is present in an amount of 80 to 85% w/w, the poloxamer 188 is present in an amount of 1 to 1.5% w/v in the nano lipid carrier; wherein an amount of phenytoin sodium ranges from 4 mg/ml to 10 mg/ml.

2. The intranasal formulation of claim 1, wherein the nano lipid carrier has a percentage entrapment efficiency (EE) from 86.69% to 95.65% and a drug loading (DL) percentage from 36.63% to 42.23% respectively.

3. The intranasal formulation of claim 1, wherein the formulation is in the form of spray or mist.

4. The intranasal formulation of claim 1, further comprising pharmaceutically acceptable carriers or excipients consisting of liquid lipid comprising triglycerides, diglycerides, monoglycerides or long chain fatty acids.

5. A method for making the intranasal formulation of claim 1, comprising:

adding phenytoin sodium to a pre-heated mixture of lipids comprising cholesterol and oleic acid, maintained at 55-60° C. to form an oil phase;

emulsifying the oil phase with a preheated aqueous phase containing 1-1.5% w/v of poloxamer 188, in deionized water at 55-60° C., to form a pre-emulsion, wherein the cholesterol is present in an amount of 15 to 20% w/w, the oleic acid is present in an amount of 80 to 85% w/w of the pre-emulsion; and ultrasonicating the pre-emulsion for 25 min at 40% amplitude for a cycle of 8 sec on and 2 sec off to form the intranasal formulation.

6. A method of treating acute epileptic emergencies comprising administering therapeutically effective dose of intra nasal formulation of claim 1, wherein the therapeutically effective dose ranges from 4 mg/kg to 10 mg/kg.

* * * * *